(12) United States Patent
Mancera Browne et al.

(10) Patent No.: US 6,381,785 B1
(45) Date of Patent: May 7, 2002

(54) DISMOUNTABLE AND ADJUSTABLE FASTENING DEVICE FOR LAYING DOWN PEDIATRIC PATIENTS IN AN INCLINED POSITION

(76) Inventors: Enrique Luis Mancera Browne; Alberto Eduardo Mancera Gonzalez, both of Unidad Fuentes Brotantes, M-12-502 Col. Miguel Hidalgo, Del. Tlalpan, C.P. 14100 (MX)

( * ) Notice: Subject to any disclaimer, the term of this patent is extended or adjusted under 35 U.S.C. 154(b) by 0 days.

(21) Appl. No.: 09/242,944
(22) PCT Filed: Aug. 28, 1997
(86) PCT No.: PCT/MX97/00024
§ 371 Date: Jun. 9, 2000
§ 102(e) Date: Jun. 9, 2000
(87) PCT Pub. No.: WO98/09587
PCT Pub. Date: Mar. 12, 1998

(30) Foreign Application Priority Data

Sep. 4, 1996 (MX) ................................................ 96352

(51) Int. Cl.[7] .................................................. A61F 5/37
(52) U.S. Cl. .................................................. 5/655; 5/424
(58) Field of Search .............................. 5/424, 494, 655

(56) References Cited

U.S. PATENT DOCUMENTS

| 4,989,286 | A | * | 2/1991 | Tucker ...................... 5/494 X |
| 5,208,925 | A | * | 5/1993 | Edlund .......................... 5/424 |
| 5,233,714 | A | * | 8/1993 | Daniel .......................... 5/655 |
| 5,400,803 | A | * | 3/1995 | Vines ........................ 5/494 X |
| 5,439,008 | A | * | 8/1995 | Bowman ................... 5/424 X |
| 5,800,368 | A | * | 9/1998 | Klingemann et al. ....... 5/655 X |

* cited by examiner

*Primary Examiner*—Michael F. Trettel
(74) *Attorney, Agent, or Firm*—Cox & Smith Incorporated

(57) ABSTRACT

This invention provides an aid to pediatric physicians and caregivers to lay an infant in incline position for use in treating various physical conditions or diseases, including gastroesophagic reflux ("GER"). The device allows for positional treatment of infants without the need for a special wedged shaped pillow or mattress. The invention allows for fast and easy access to the infant in case of urgency, but still avoids the possibility of the infant releasing himself. The device can be removed for washing or replacement of a new device, depending upon the size of the infant. The device allows the infant to be laid prone, supine, or laterally.

3 Claims, 12 Drawing Sheets

DISMOUNTABLE AND ADJUSTABLE FASTENING DEVICE FOR LAYING DOWN PEDIATRIC PATIENTS IN AN INCLINED POSITION

BACKGROUND OF THE INVENTION

1. Field of the Invention

In treating pediatric patients with various diseases that may include post-operative, ophthalmologic, cardiological, neurological, and gastro-entrological, including gastroesophagic reflux ("GER"), the treatment may require the patient to be placed in an incline position. This physical position therapy utilizes the force of gravity to maintain bodily fluids and tissues down in the body. Typically, physicians and patients improvise treatments that include restraints and blockages that are not always safe or effective. Additionally, one treatment requires keeping the baby constantly seated in a baby chair, however this procedure, besides being very uncomfortable, may result contraindicated.

2. Description of the Related Art

U.S. Pat. No. 4,862,535 issued to Roberts, discloses a therapeutic device for positional treatment of GER which consists on an anti-reflux pillow, comprising a wedge shaped support pillow having an inclined infant-supporting surface, with a diaper-like infant torso encircling sling, attachable to the infant supporting surface of the support pillow. Two parallel strips of VELCRO® fastener adhesive material are attached at the opposite lateral edges of the torso encircling sling and the inclined surface of the supporting pillow. The infant is secured inside the torso encircling sling with two parallel sets of snap fasteners that close the sides of the torso encircling sling. The wedge shaped supporting pillow is soft and deformable to create a cavity where the infant is placed.

Since the infant in the Roberts disclosure is attached to the supporting surface of the supporting pillow by the torso, the device therein permits free movement of the arms and legs but not of the mentioned attached torso. The device in Roberts does not permit the use of bottom sheets under the infant. In addition, the infant in the Roberts disclosure is uncomfortable since he/she is obviously prevented from moving his/her torso while being attached to the supporting pillow precisely by the torso.

Roberts describes, in the background of the patent document, that the arrangement is intended for use with weak and tiny infants placed in intensive care nurseries. However, not all infants that need this kind of positional therapy are tiny and weak, and not all of them are attended at intensive care nurseries. If a bigger or stronger infant is placed on the Roberts' arrangement, the infant will surely pull or move forcefully enough to unfasten the sets of simple snap fasteners that close the sides of the torso encircling sling and/or the VELCRO® fastening strips that fasten the torso encircling sling to the infant supporting surface of the mentioned supporting pillow. A strong restless infant may also pull the sling or lateral fastener means with his own hands and fall from the pillow.

Yet another problem with the Roberts pillow is that the infant can not be placed in a lateral position as many physicians prefer. This system necessitates the use of a special wedge shaped pillow or support system with the torso encircling sling, thus making it more complicated and expensive.

Further, a danger arises when an infant is laid prone on a surface like the Roberts' pillow where the infant's face may sink into the pillow and suffocate if breathing is obstructed. This danger is magnified if one considers the possibility of the infant vomiting with or without GER (gastroesophagic reflux).

Another danger with the Roberts' arrangement is the support system or wedge shaped pillow being filled with Styrofoam® balls. This material is so light that an uneasy infant attached to it making a strong lateral movement may cause the entire device to turn upside down, thus traps the infant inside.

There is a great need for an infant positioning container that is safe, comfortable and inexpensive, and suitable for tiny or big, weak or strong, calm or uneasy infants, staying at home or in an intensive care nursery. It would be desirable for the container to allow easy and quick access to the infant in case of urgency, while being usable on any bed, cradle, crib, baby basket, incubator mattress, or on a special wedge shaped mattress, if desired. It would be securable if the container allowed the infant be laid prone supine or lateral, allowed the infant to move its legs, arms or torso freely, and allowed the use of a removable bottom sheet under the infant. It would be useful if no matter how big, heavy, strong or restless the infant could be, he/she would not be able to release himself with his hands, movements or weight. It would be desirable if the container is adjustable, easy to change and washable, or, in the alternative, made of disposable materials. It would further be important for the container to be inexpensive and simple to construct compared to the existing systems.

SUMMARY OF THE INVENTION

The main objective of the present invention is to aid pediatric physicians and caregivers along with parents and relatives of infants to safely lay the infants in an inclined position, as shown in FIGS. 11 and 12, whether they are placed in a basket, incubator, bassinet, cradle or on bed mattress at a nursery or at home, thus overcoming the problems and insufficiencies of prior inventions.

Another objective of the present invention is to be useful for the positional treatment of tiny and weak, heavy, strong or big infants on their bed, cradle, baby basket, incubators, bassinets, mattresses, without the need for a special wedged shaped pillow or mattress, if used with the strap system shown in FIGS. 4, 5 and 12, or with the mattress cover option shown in FIGS. 6, 7 and 11.

Another objective of this invention, is to permit fast and easy access to the infant in case of urgency, but still avoiding the possibility that the infant could release himself with his own hands, movements or weight, no matter how big, heavy, strong or uneasy the infant is.

Another objective of the present invention is to permit the caregivers to remove the device easily for washing or moving the baby and device together, or to replace the device with a clean one or one of a different size, depending upon the size of the infant, as shown in FIGS. 1, 2 and 3.

Another objective of the present invention is to permit the infant to be laid prone, supine or laterally.

Another objective is to permit the infant to move his/her arms, legs and torso freely, letting the infant feel less confined, more comfortable and avoid the danger of falling or moving from the desired position.

Another objective is to permit the device to be graduated while the infant grows, as shown in FIG. 8.

Another objective is to permit the use of disposable materials in the construction of the infant fastening device, when convenient.

These and other objectives of the present invention are made possible with the provision of an infant fastening device, which includes a fastening system that can be attached to any cradle, bed or basket, ordinary or special mattress at home, or in warmers and isolators in nurseries and hospitals.

This invention is intended to fulfill the need for an appropriate tool for the treatment of infants that require the above described kind of positional therapy.

DESCRIPTION OF THE INVENTION

Figure 1:
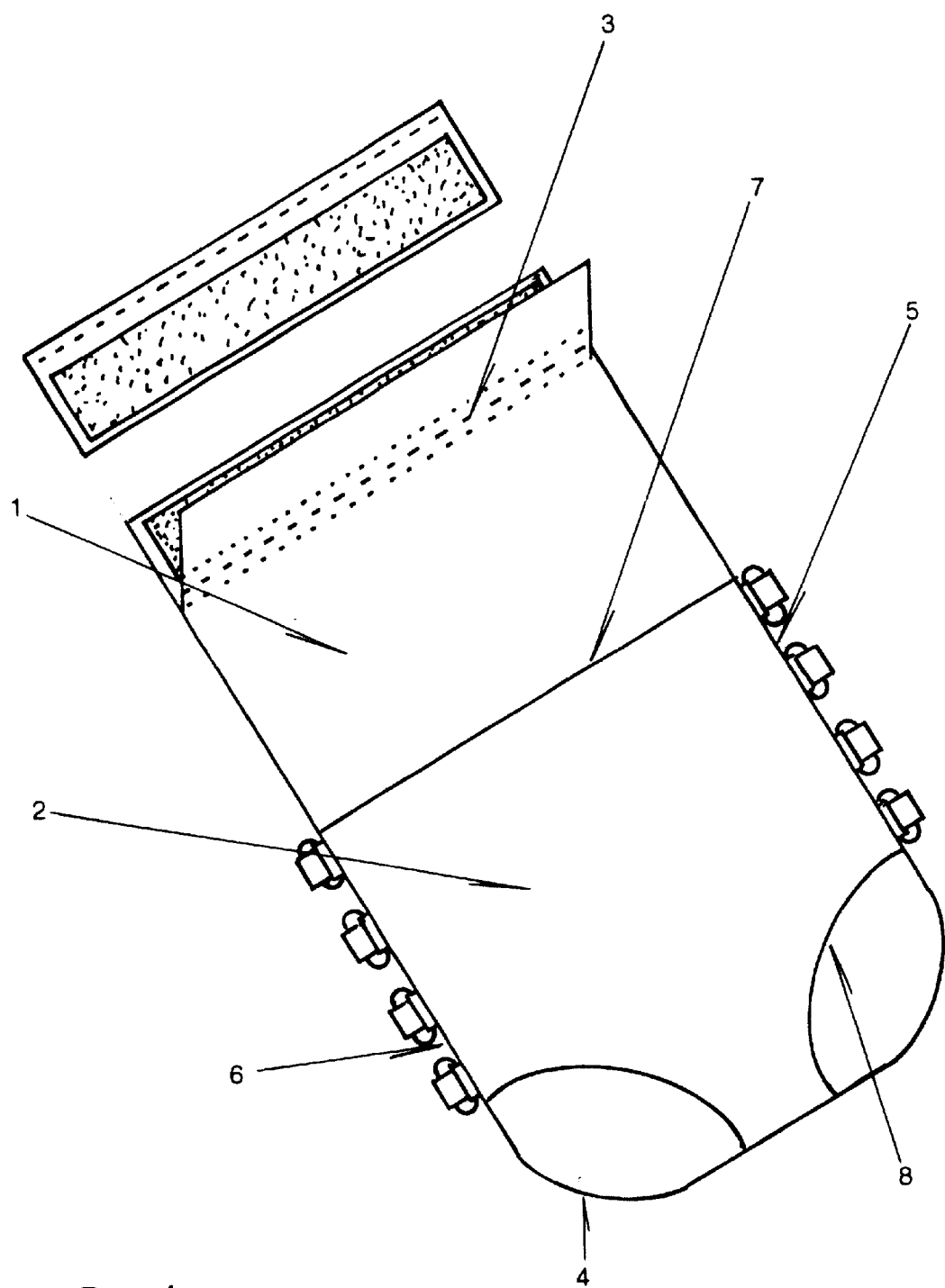
FIG. 1 is a perspective view of the bag shaped infant container of the present invention closed on a frontal view to show its main parts.

FIG. 1 is a perspective view of the bag shaped infant container of the present invention closed on a frontal view to show its main parts.

In FIG. 1, the following identified elements are shown:
  (1) Rear or back rectangular long piece.
  (2) Front shorter rectangular piece.
  (3) Superior or top edge of the back piece, with the winged "V" shaped attaching arrangement opened.
  (4) Inferior or bottom edge of the back piece showing the rounded corners.
  (5) & (6) Lateral sides of rear (1) and front (2) rectangular pieces.
  (7) Superior edge of the rectangular shorter front piece (2).
  (8) Arcuate cutouts on the inferior edge of the front shorter rectangular piece (2).

Figure 2:
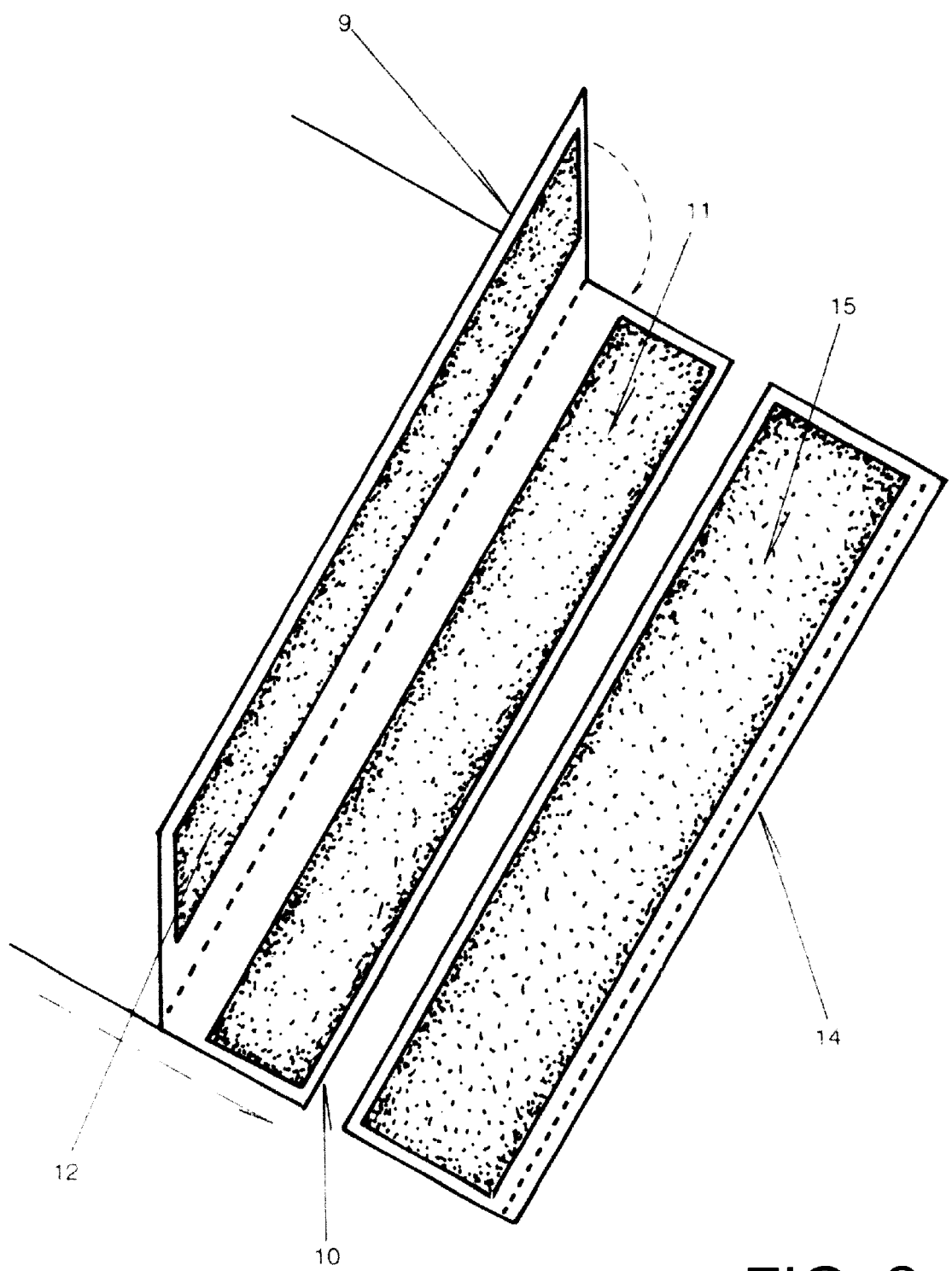
FIG. 2 is a detailed perspective view of the superior winged, "V" shape, sandwich type fastening arrangement of the infant container.

FIG. 2 is a detailed perspective view of the superior winged, "V" shape, sandwich type fastening arrangement of the infant container.

In FIG. 2 the following identified elements are shown:
  (9) & (10) Exterior surfaces of the winged rectangular shaped pieces, attached to the superior edge of the back piece (1) of the infant container (not shown), forming a "V" shape opened to show both inner surfaces.
  (11) & (12) Strips of Velcro® fastener plush attaching material, applied along the interior surface of the winged "V" shape, superior attaching arrangement.
  (14) Superior rectangular shaped, fastening tongue.
  (15) Strips of Velcro® fastener hook adhesive material applied along the exterior surfaces of the superior, rectangular shape fastening tongue (opposite surface not shown.)

Figure 3:
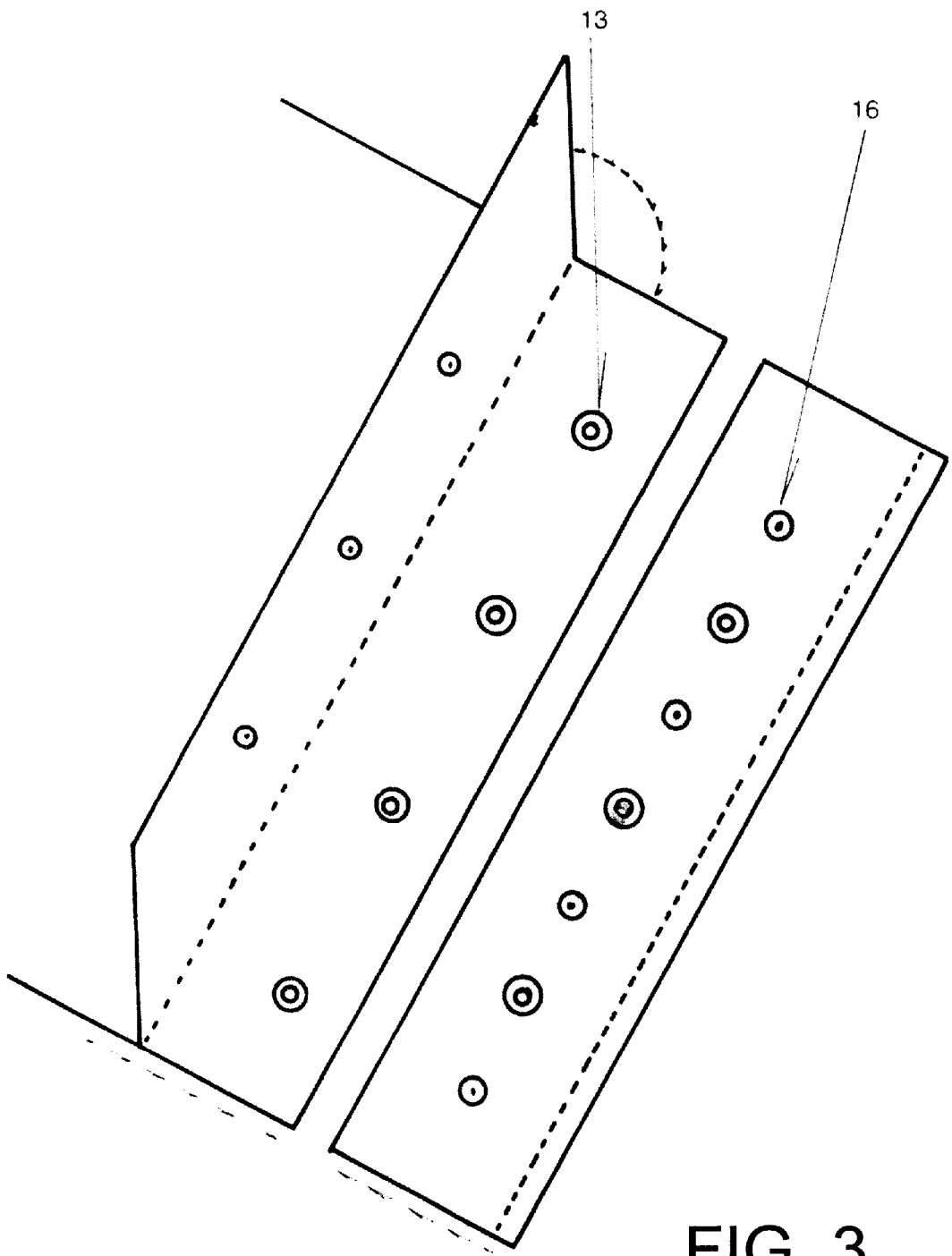
FIG. 3 is a detailed perspective view of the superior winged "V" shape, sandwich type fastening arrangement, with snap clasps instead of Velcro® fasteners attaching material.

FIG. 3 is a detailed perspective view of the superior winged "V" shape, sandwich type fastening arrangement, with snap clasps instead of Velcro® fastener attaching material.

In FIG. 3 the following additional examples are shown:
  (13) Clasps attached to the inner surface of the winged "V" shape, superior fastening arrangement.
  (16) Clasp counters, attached to the exterior surfaces of the rectangular shaped attaching tongue (opposite surface not shown.)

Figure 4:
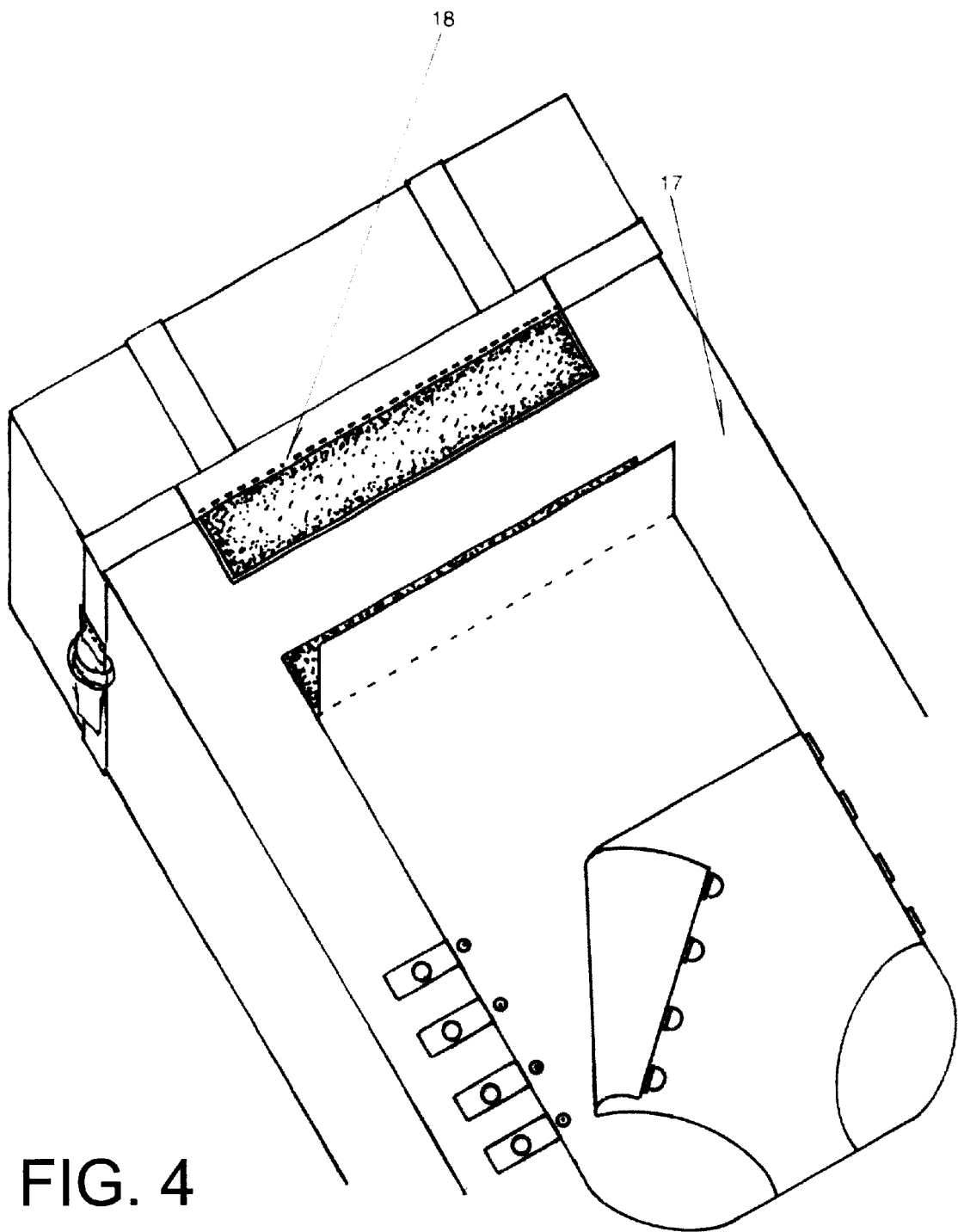
FIG. 4 is a perspective view showing the rectangular shaped attaching tongue of the present invention mounted on the superior side of a common inclined mattress with the strip attaching system option.

FIG. 4 is a perspective view showing the rectangular shaped attaching tongue of the present invention mounted on the superior side of a common inclined mattress with the strip attaching system option.

In FIG. 4 the following additional elements are shown:
  (17) Superior elevated side of a common mattress.
  (18) Tongue and strip mounting system, attached to a mattress.

Figure 5:
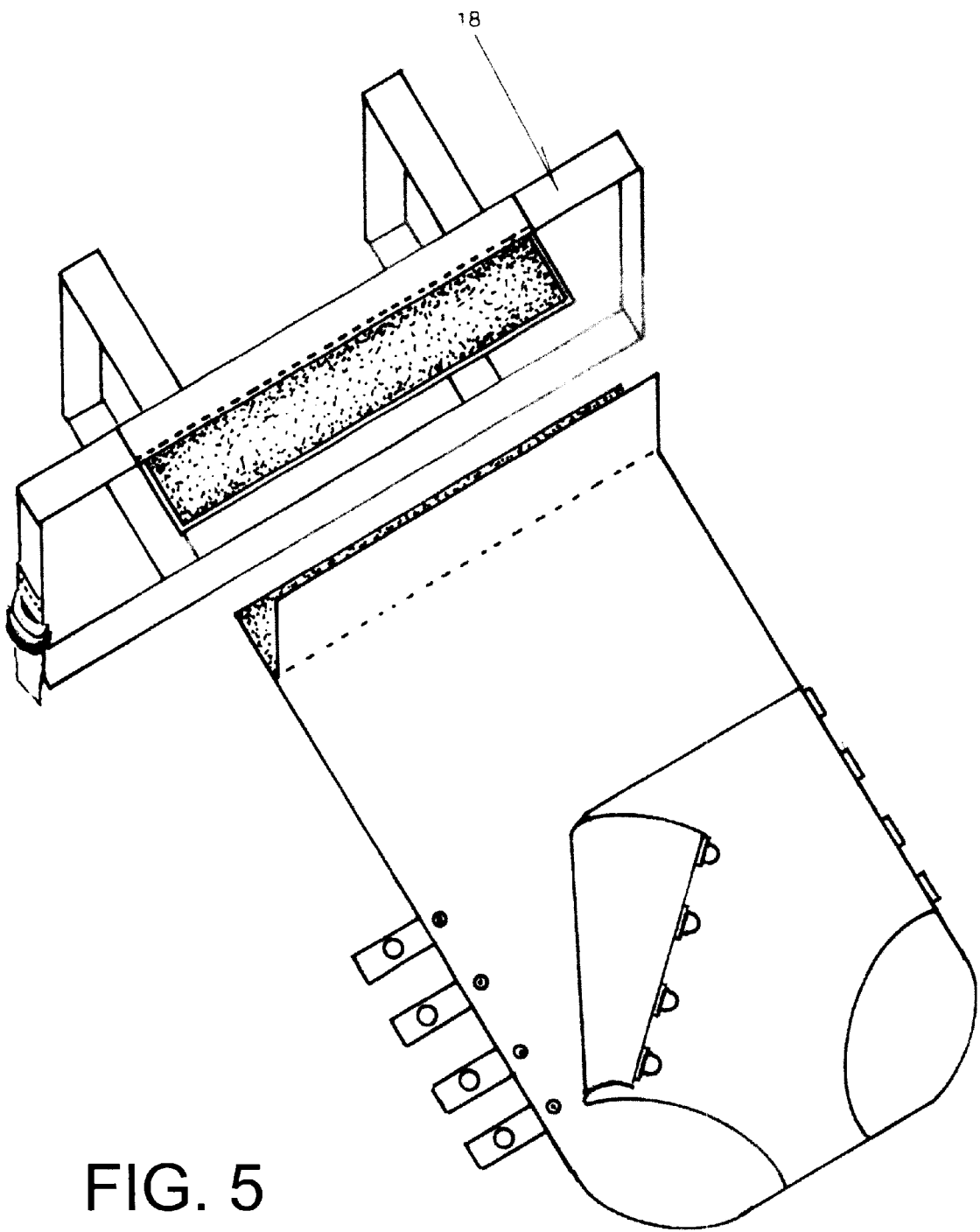
FIG. 5 is a perspective view of the complete strip system without mattress.

FIG. 5 is a perspective view of the complete strip system without mattress.

Figure 6:
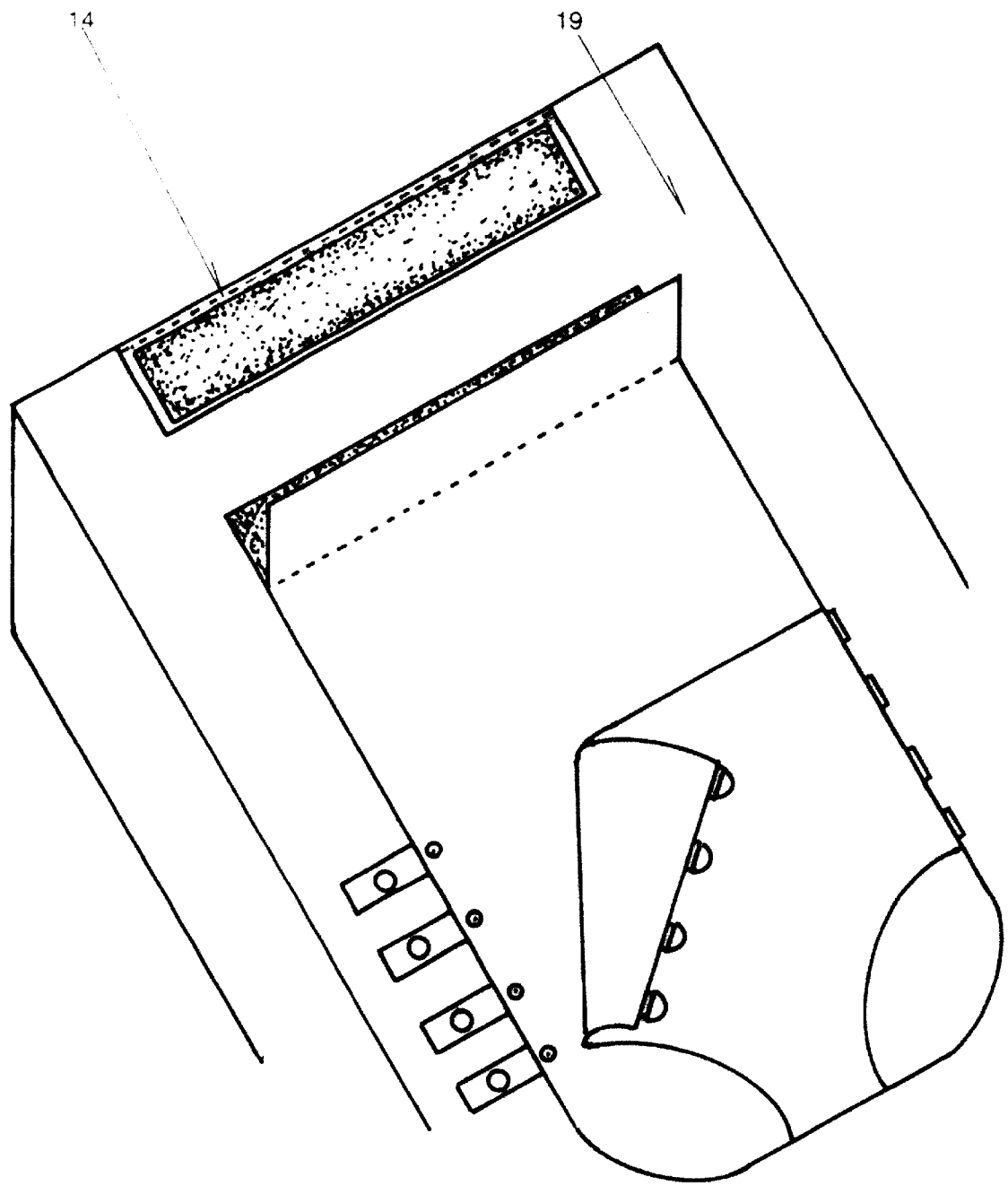
FIG. 6 is a perspective view of the rectangular shaped attaching tongue shown sewn to the superior side of the cover of a common mattress.

FIG. 6 is a perspective view of the rectangular shaped attaching tongue shown sewn to the superior side of the cover of a common mattress. In FIG. 6 the following additional element is shown:
  (19) mattress cover.

Figure 7:
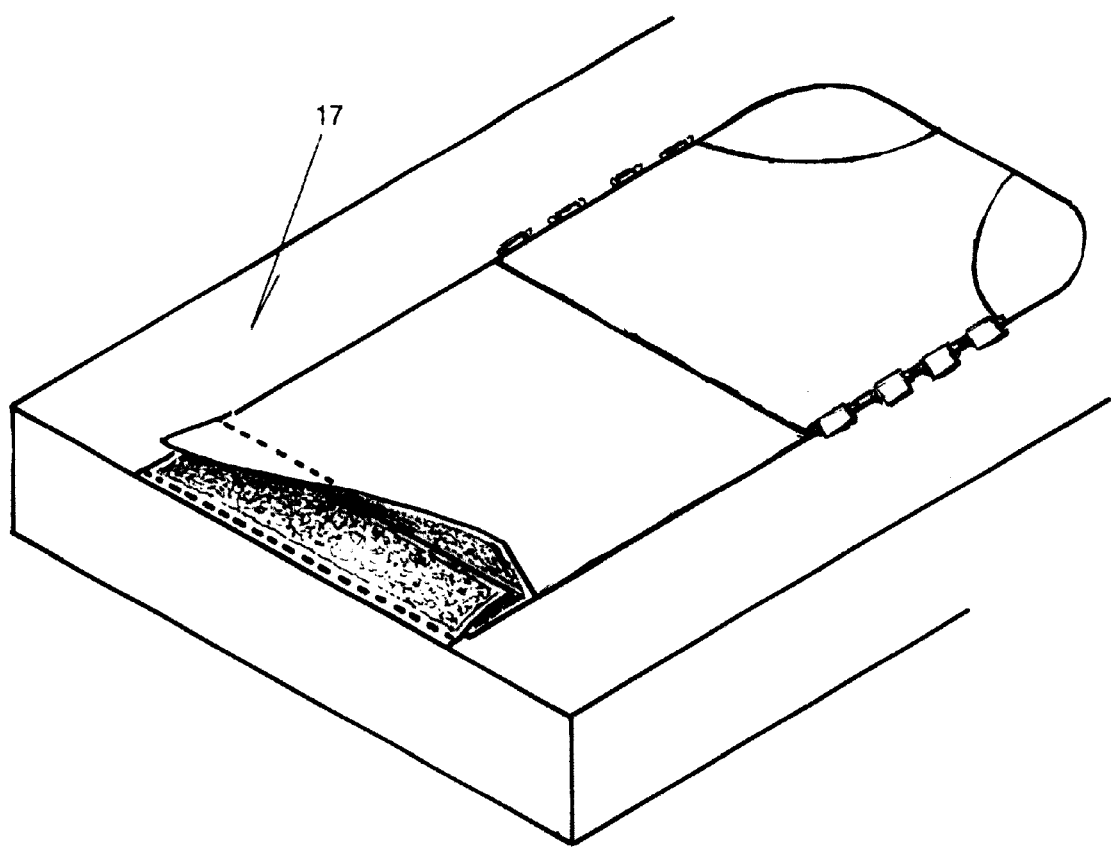
FIG. 7 presents a perspective rear view of the winged "V" shaped sandwich type superior fastener, closed over the inner attaching tongue.

FIG. 7 presents a rear perspective view of the winged "V" shaped sandwich type superior fastener, closed over the inner attaching tongue.

Figure 8:
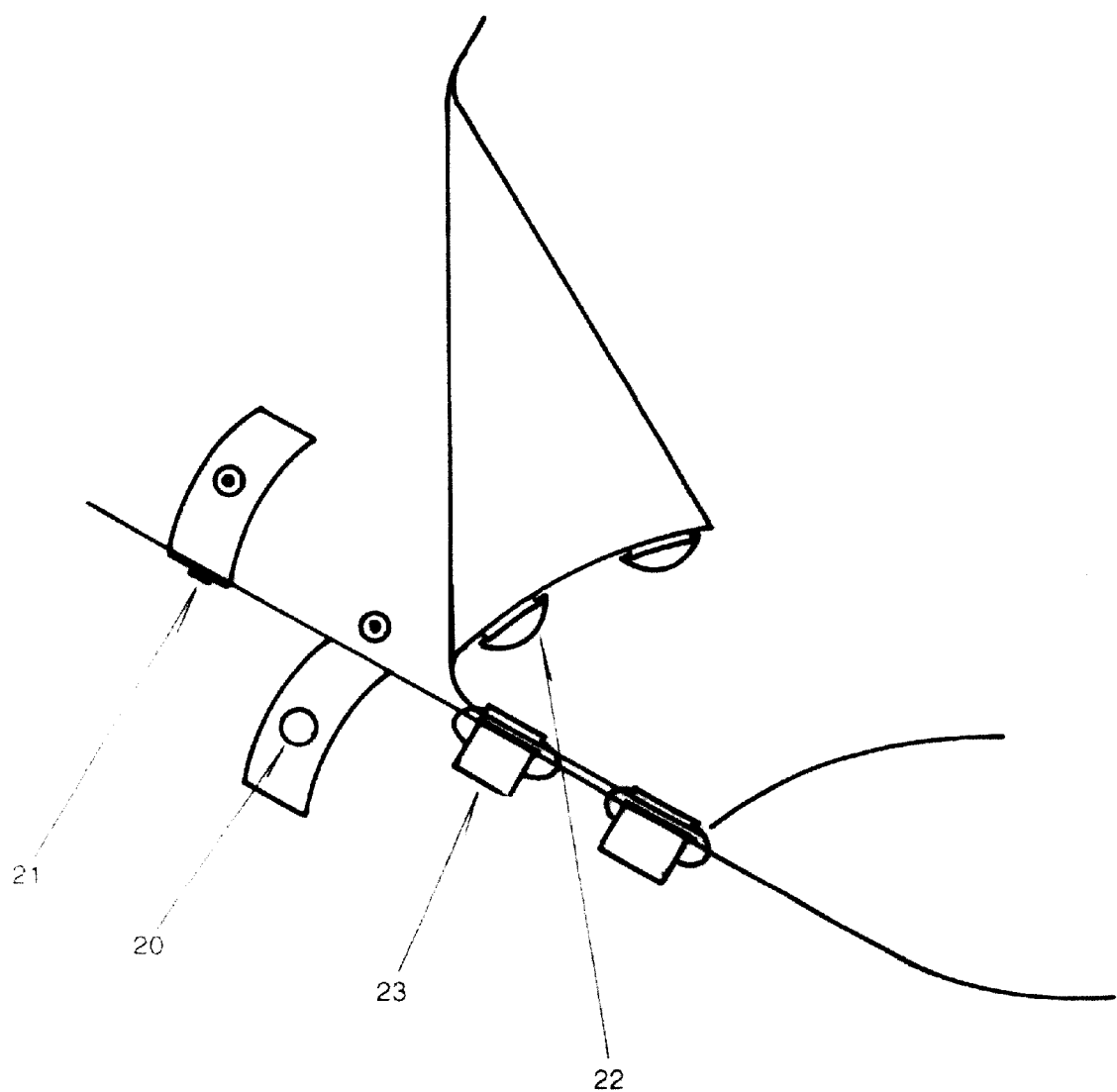
FIG. 8 presents a detailed perspective view of one lateral edge of the infant container showing the strips with clasps and rings attachment system, also showing how it can be adjusted up or down.

FIG. 8 presents a detailed perspective view of one lateral edge of the infant container showing the strips with clasps and rings attachment system, also showing how it can be adjusted up or down.

In FIG. 8 the following additional elements are shown:
  (20) Strip with snap type clasp.
  (21) Snap type clasp counter section applied near the junction of the strip with the lateral edge of the back piece of the infant container.
  (22) Rings attached to the lateral edge of the front piece of the infant container.
  (23) Strip with clasp and ring attachment arrangement FIG. 9 is a perspective view of the bag shaped infant container, opened to show all of its pieces extended.

Figure 9:
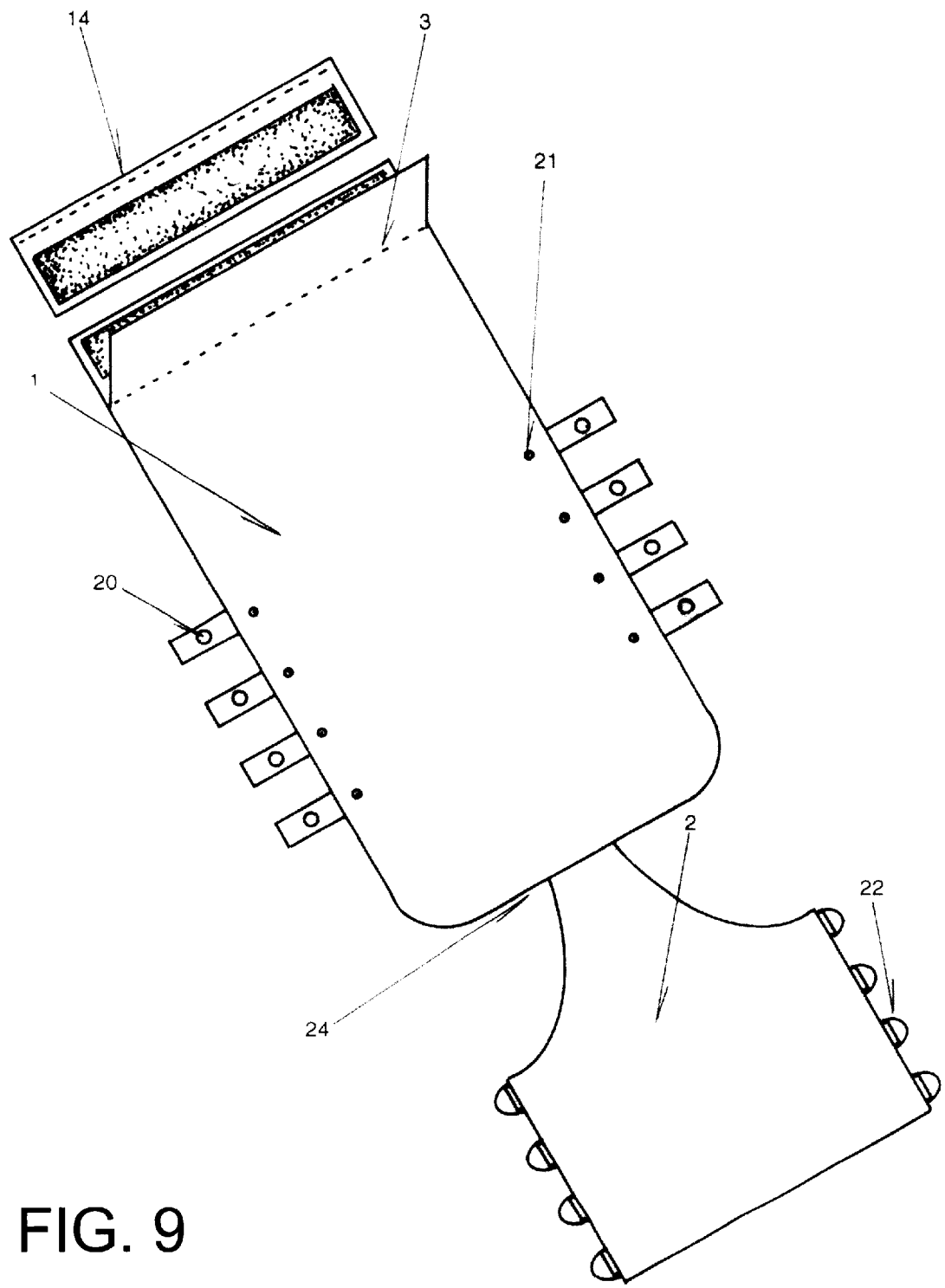
FIG. 9 is a perspective view of the bag shaped infant container, opened to show all of its pieces extended.

In FIG. 9 the following additional elements are shown:
  (24) The central portion left between the arcuate cutouts of the front piece, attached to a central position between the rounded corners of the bottom edge of the back piece of the infant container.

Figure 10:
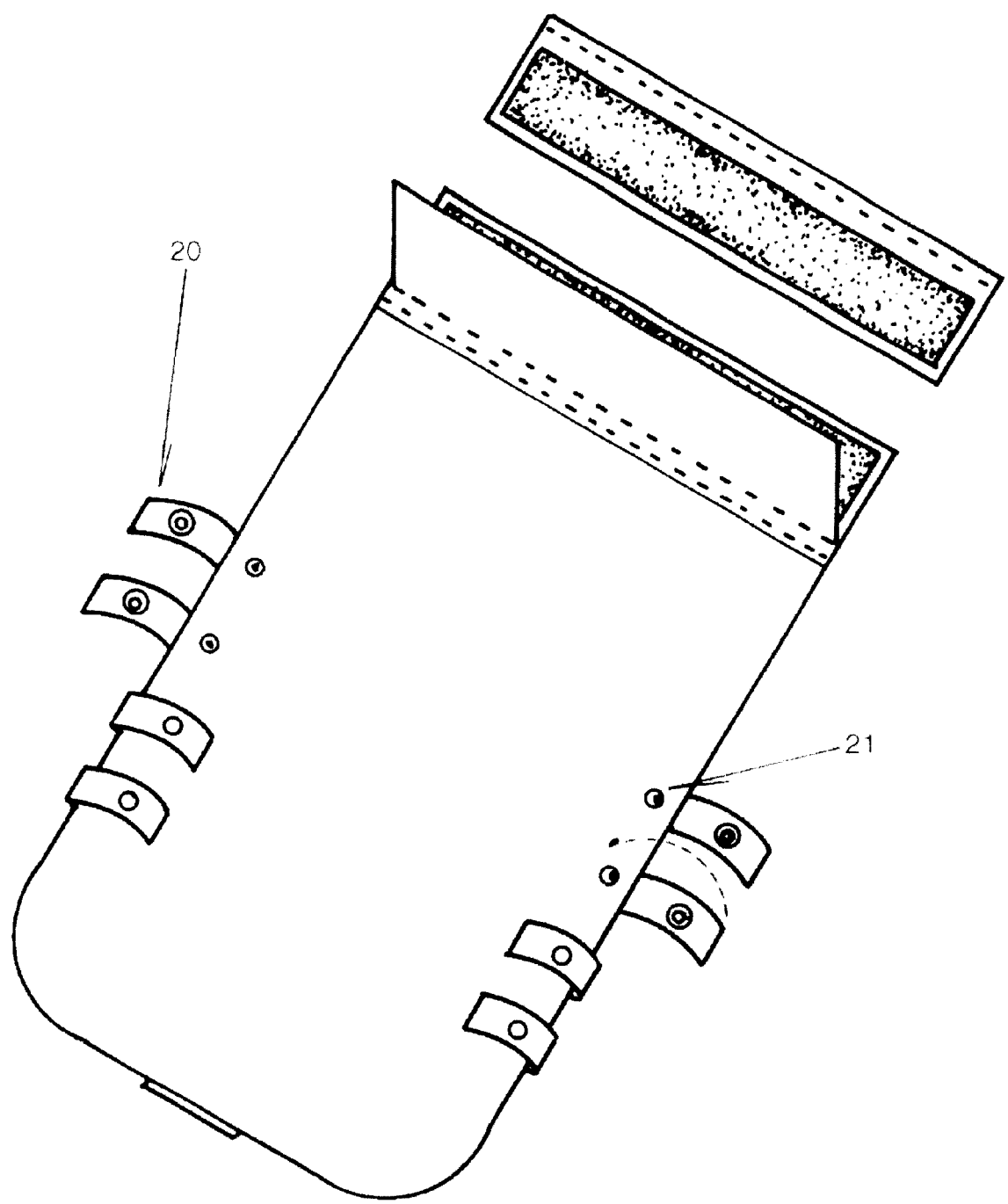
FIG. 10 is a perspective view of a closed infant container, turned back to show four lateral strips with clasps snapped back and four lateral strips with clasps snapped.

FIG. 10 is a perspective view of a closed infant container, turned back to show four lateral strips with clasps snapped back and four lateral strips with clasps unsnapped.

Figure 11:
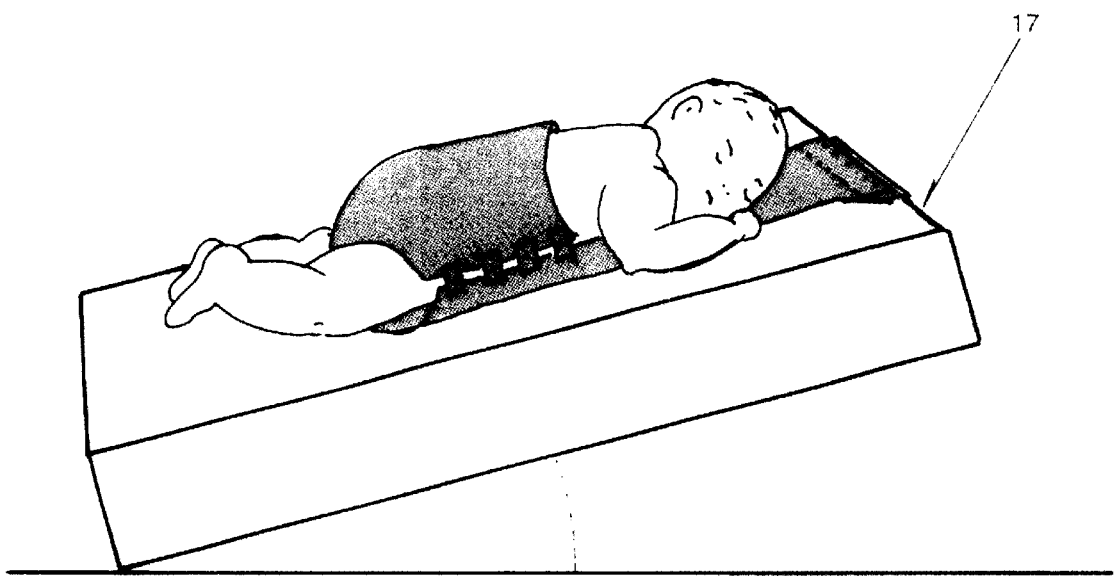
FIG. 11 is a perspective view showing the use of the infant container, with an infant laying prone on it, over a common inclined mattress.

FIG. 11 is a perspective view showing the use of the infant container, with an infant laying prone on it, over a common inclined mattress.

Figure 12:
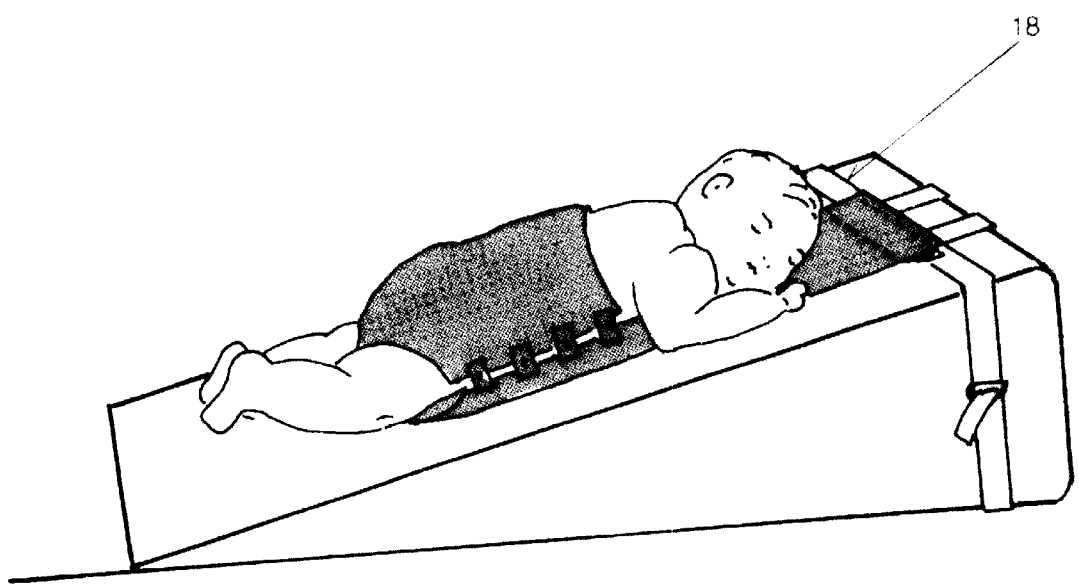
FIG. 12 is a perspective view, presenting the infant container attached to a special wedge shaped mattress, with the strip system of the present invention.

FIG. 12 is a perspective view, presenting the infant container attached to a special wedge shaped mattress, with the strip system of the present invention.

The present invention consists of an infant container, with the shape of a bag made with cloth or disposable material as shown in FIG. 1. This bag shaped infant container is made with two main pieces, a rear piece (1) and a front piece (2). The rear piece (1) of the container is longer than the front piece (2), and is rectangular in shape, comprising a superior or top side (3), an inferior or bottom side (4) with rounded corners and two lateral sides (5) and (6). The front piece (2) is shorter than the rear piece, but is also rectangular with a superior or top side (7) and inferior or bottom side, with two arcuated cutouts (8) on each corner and two lateral sides that coincide with the lateral sides (5) and (6) of the rear piece (1).

Along the superior side (3) of the mentioned rear piece (1) is a winged "V" shaped "sandwich type" fastening arrangement detailed in FIGS. 2, 3 and 7. This arrangement is made of two rectangular pieces of cloth or disposable material (9) and (10), attached along the superior edge of the rectangular rear piece (3), forming a winged "V" shaped arrangement. This so-called winged "V" shaped arrangement has two exterior surfaces (9) and (10) and two interior surfaces (11) and (12). Applied along the mentioned interior surface of each "wing" of the "V" shaped arrangement is a strip of the plush side of VELCRO® fastener adhesive material (11) and (12) or in an alternative embodiment, a set of clasps (13), as shown in FIG. 3.

A rectangular shaped tongue (14) made of cloth or disposable material having two sides or opposite surfaces along each side or surface of the mentioned rectangular shaped tongue (14) is applied a strip of VELCRO® fastener hook side adhesive material (15) or in an alternative embodiment a set of clasps (16), as shown in FIG. 3. The rectangular shaped tongue (14), covered with VELCRO® fastener hooks or with clasps applied on its surfaces, is attached to the elevated side of an inclined mattress (17) as shown in FIG. 4, by a strip fastening (18) in arrangement FIGS. 4, 7 and 11, or sewn to the cover of the mattress (19) in FIGS. 6, 7 and 11.

VELCRO® fastener is an adhesive stripped material, made of two strips that attach to each other, one of the strips is made on its adhesive surface of a "plush-like" material. The other strip is made on its adhesive surface, of a hook-like material, when these surfaces of the mentioned hook and plush strips are joined together, they attach to each other.

Once the rectangular shaped tongue (14) is sewn to the superior side of the cover on an inclined mattress or attached to it with the fastening strip arrangement, the superior edge of the rear rectangular piece is opened to expose the "V" shaped fastening arrangement, which is inserted in the fastening tongue (14). The wings are then closed over as shown in FIG. 7. This double surface, positioned high on the infant container and only on the superior side of it, allows all of the torso of the infant free to move, permits the use of bottom sheets under the infant and leaves the infant comfortable, permitting the infant to lay laterally and allowing the fast and easy release of the infant if necessary.

Lengthwise along the lateral edges of the rear piece of the infant container as best seen in FIGS. 8, 11 and 10, is placed a set of strips with a snap clasp on each strip (20). Lengthwise along the lateral sides of the front piece of the infant container as best seen in FIGS. 8 and 9, is placed a set of rings (22). Near the union of each strip (20) with snap clasp, on the edge of the mentioned rear piece of the infant container, is placed a clasp counter (21). The strips with clasps means (20) are passed through the inside of the rings (22) and turned back to be attached to the counter of the clasp means, placed on the lateral edge of the rear piece (23) of the infant container. This strip with clasp and ring fastening system is highly resistant and depending on the number of strips with clasp and rings that are attached, the front piece can be lengthened while the infant grows.

What I claim is:

1. An adjustable and releaseable holding device for positioning an infant on an inclined platform, the holding device comprising:

(a) a top panel comprising a generally rectangular sheet of cloth fabric or disposable material, said top panel having an upper and a lower edge and two lateral side edges, said lower edge defining a pair of arcuate cutouts for receiving said infant's legs, said top panel further comprising a plurality of spaced rings attached to and positioned along each of said two lateral side edges; and (b) a bottom panel comprising a generally rectangular sheet of cloth fabric or disposable material, said bottom panel having an upper and a lower edge and two lateral side edges, said bottom panel positioned adjacent said top panel such that said lower edge and said two lateral side edges of each of said panels coincide, said bottom panel being generally longer than said top panel such that said upper edge of said bottom panel extends above said upper edge of said top panel, said bottom panel further comprising a plurality of spaced strap/snap connectors attached to and positioned along each of said two lateral side edges, each of said strap/snap connectors comprising a strap element aligned with and passable through a corresponding one of said rings positioned on said top panel, and a mating pair of snap connector elements retaining said strap element in place after passage through said corresponding ring on said top panel.

2. The device of claim 1 wherein said bottom panel further comprises a fastening strip for securing said device to said inclined platform, said fastening strip comprising first and second wings, said wings comprising generally rectangular sections of cloth fabric or disposable material secured to each other and to said upper edge of said bottom panel, said wings each having an interior face and an exterior face and together forming a winged opening having a "V" shaped cross section, each of said interior faces of said wings further comprising an attachment surface.

3. The device of claim 2 wherein said fastening strip further comprises a fastening tongue, said fastening tongue fixed to said inclined platform and positioned to be received by said wings when said device is positioned on said platform, said fastening strip comprising a generally rectangular section of cloth fabric or disposable material and having two faces, each of said faces further comprising an attachment surface mateable with said attachment surfaces of said interior faces of said wings, wherein said wings may be folded open to receive said fastening tongue and subsequently folded closed around said fastening tongue so as to mate said attachment surfaces of said fastening tongue with said attachment surfaces of said wings.

* * * * *